(12) United States Patent
Kim

(10) Patent No.: US 12,262,759 B2
(45) Date of Patent: Apr. 1, 2025

(54) UNDERWEAR FOR WOMEN WITH LEAK-PROOF FUNCTION TIGHTLY FITTING TO HUMAN INTERGLUTEAL CLEFT

(71) Applicant: DOUBLE SENSE INC., Seoul (KR)

(72) Inventor: Mi Hee Kim, Seoul (KR)

(73) Assignee: DOUBLE SENSE INC., Seoul (KR)

( * ) Notice: Subject to any disclaimer, the term of this patent is extended or adjusted under 35 U.S.C. 154(b) by 0 days.

(21) Appl. No.: 18/028,562

(22) PCT Filed: Oct. 28, 2022

(86) PCT No.: PCT/KR2022/016673
§ 371 (c)(1),
(2) Date: Mar. 27, 2023

(87) PCT Pub. No.: WO2023/080557
PCT Pub. Date: May 11, 2023

(65) Prior Publication Data
US 2024/0358091 A1  Oct. 31, 2024

(30) Foreign Application Priority Data
Nov. 3, 2021  (KR) .......................... 10-2021-0150012

(51) Int. Cl.
*A41B 9/12* (2006.01)
*A41B 9/04* (2006.01)
(Continued)

(52) U.S. Cl.
CPC .................. *A41B 9/12* (2013.01); *A41B 9/04* (2013.01); *A41B 9/14* (2013.01); *A61F 13/47218* (2013.01); *A41B 2300/332* (2013.01)

(58) Field of Classification Search
CPC .... A41B 9/12; A41B 9/04; A41B 9/14; A41B 2300/332; A61F 13/47218
See application file for complete search history.

(56) References Cited

U.S. PATENT DOCUMENTS 1,577,409 A * 3/1926 Rand .................. A41B 9/04
2/407
2,250,218 A * 7/1941 Cadous .................. A41B 9/04
2/401
(Continued)

FOREIGN PATENT DOCUMENTS

JP  2002371402 A  * 12/2002
KR  10-2014032 B1  10/2019

*Primary Examiner* — Khaled Annis
(74) *Attorney, Agent, or Firm* — CANTOR COLBURN LLP

(57) ABSTRACT

Underwear according to the present disclosure may include an underwear portion and a band portion. The underwear portion may include a back side as an opposite side of a front side, in which the back side includes a cleft-fitting region that deforms to conform to the shape of an intergluteal cleft after underwear is worn. The band portion may include a cleft-fitting band disposed in a corresponding direction along the cleft-fitting region and a support portion supporting the cleft-fitting band.

According to the present disclosure, underwear for women with a leak-proof function tightly fitting to a human intergluteal cleft can dramatically prevent the body fluids generated during menstruation from leaking through, by using the band portion including the cleft-fitting band disposed in a corresponding direction along the cleft-fitting region and the support portion supporting the cleft-fitting band.

8 Claims, 12 Drawing Sheets

(51) Int. Cl.
*A41B 9/14* (2006.01)
*A61F 13/472* (2006.01)

(56) References Cited

U.S. PATENT DOCUMENTS

| | | | | |
|---|---|---|---|---|
| 2,522,510 | A * | 9/1950 | Fridolph | A41B 9/04 2/407 |
| 4,597,110 | A * | 7/1986 | Smith, Sr. | A41B 9/007 2/408 |
| 4,612,674 | A * | 9/1986 | Hashimoto | A41B 9/004 2/406 |
| 9,713,351 | B2 * | 7/2017 | Wexler | A41D 1/06 |
| 11,911,247 | B2 * | 2/2024 | Hopkins | A61F 13/53418 |
| 2002/0016580 | A1 * | 2/2002 | Wada | A41B 9/12 604/385.24 |
| 2003/0204898 | A1 * | 11/2003 | Blanco | A41B 9/002 2/406 |
| 2006/0264881 | A1 * | 11/2006 | Carstens | A61F 13/4752 604/402 |
| 2006/0264884 | A1 * | 11/2006 | Carstens | A61F 13/4704 604/402 |
| 2008/0268749 | A1 * | 10/2008 | Oyama | A41C 1/003 450/99 |
| 2009/0139003 | A1 * | 6/2009 | Lee | A41B 9/12 2/400 |
| 2010/0175170 | A1 * | 7/2010 | Dye | A41B 9/004 604/367 |
| 2010/0175171 | A1 * | 7/2010 | Dye | A41B 9/04 2/406 |
| 2010/0275349 | A1 * | 11/2010 | Wilson, II | A41D 13/0506 2/466 |
| 2012/0253304 | A1 * | 10/2012 | Scott | A61F 13/15699 493/379 |
| 2014/0230825 | A1 * | 8/2014 | Zaltsberg | A61F 13/66 128/835 |
| 2014/0237704 | A1 * | 8/2014 | Mehrabian | A41B 9/02 2/403 |
| 2016/0050977 | A1 * | 2/2016 | Jakob | A41B 9/10 2/211 |
| 2016/0353806 | A1 * | 12/2016 | Mendonça Coutsoumbos | A41B 9/04 |
| 2017/0007469 | A1 * | 1/2017 | Medley | A41B 9/04 |
| 2022/0202550 | A1 * | 6/2022 | Cornier | A41B 9/04 |
| 2022/0256938 | A1 * | 8/2022 | King | A41B 9/12 |
| 2022/0331138 | A1 * | 10/2022 | Behn | A61F 5/30 |

* cited by examiner

FIG. 6

| RATIO (H2/H1) | FOREIGN SENSATION (EP) SCORE |
|---|---|
| FIRST RANGE (3~4) | 15 |
| SECOND RANGE (2~3) | 20 |
| THIRD RANGE (1~2) | 20 |

FIG. 7

| RATIO (H2/H1) | LEAK-PROOF SCORE (SP) |
|---|---|
| FIRST RANGE (3~4) | 20 |
| SECOND RANGE (2~3) | 20 |
| THIRD RANGE (1~2) | 10 |

UNDERWEAR FOR WOMEN WITH LEAK-PROOF FUNCTION TIGHTLY FITTING TO HUMAN INTERGLUTEAL CLEFT

TECHNICAL FIELD

The present disclosure relates to underwear for women with a leak-proof function tightly fitting to a human intergluteal cleft.

BACKGROUND ART

In general, underwear for women may be one of the essential articles of clothing to be worn on body. On the other hand, women often experience pathological secretions caused by leukorrhea, etc., and various physiological secretions secreted during ovulation or after menstruation leaking to contaminate the vulva or its surroundings. In addition, many surveys indicate that many women experience embarrassing situations when body fluids leak out of their underwear during their menstrual periods. In recent years, as women's interest in hygiene increases, various studies are being conducted to solve these problems that occur during menstruation.

SUMMARY OF INVENTION

Technical Problem

The technical problem to be achieved by the present disclosure is to provide underwear for women with a leak-proof function tightly fitting to a human intergluteal cleft, capable of preventing body fluids generated during menstruation from leaking through, by using a band portion including a cleft-fitting band disposed in a corresponding direction along a region (hereinafter referred to as a "cleft-fitting region") that deforms to conform to the shape of an intergluteal cleft and tightly fits thereto, and a support portion supporting the cleft-fitting band.

Technical Solution

In order to solve the above and other problems, underwear according to the present disclosure may include an underwear portion and a band portion. The underwear portion may include a back side as an opposite side of a front side, in which the back side may include a cleft-fitting region that deforms to conform to the shape of an intergluteal cleft and tightly fits thereto. The band portion may include a cleft-fitting band disposed in a corresponding direction along the cleft-fitting region and a support portion supporting the cleft-fitting band.

In one embodiment, the cleft-fitting region may be formed with a contractible portion so as to allow tight fit to the intergluteal cleft.

In one embodiment, the contractible portion may be formed by a mechanical or chemical shrinkage processing, or by pleating, wherein pleats may be shirring pleats, gathered pleats, dart pleats, politz pleats, ribbed pleats, mechanical pleats, pleats caused by contractible or elastic bands, and combinations thereof.

In one embodiment, one end of the cleft-fitting band may be attached to and detached from one end of the cleft-fitting region, and a first end of the support portion may be attached to and detached from a first seam where the front side and the back side of the underwear portion meet, and a second end of the support portion may be attached to and detached from a second seam where the front side and the back side of the underwear portion meet.

In one embodiment, the front side may include a plurality of coupling regions to and from which the first end of the support portion and the second end of the support portion are attached and detached.

In one embodiment, a foreign sensation score indicating a degree of foreign sensation may vary depending on a ratio between a length from one end of the cleft-fitting band to one end of the band portion in a third direction, and a length of the cleft-fitting band.

In one embodiment, a leak-proof score indicating a degree of ability to prevent leaks of body fluids may vary depending on a ratio between a length from one end of the cleft-fitting band to one end of the band portion in a third direction, and a length of the cleft-fitting band.

In one embodiment, a value obtained by dividing a length from one end of the cleft-fitting band to one end of the band portion in a third direction by a length of the cleft-fitting band may be between 2 and 3.

In one embodiment, a contractible portion of the cleft-fitting region may be contracted by 30 to 40% compared to before the contractible portion was formed.

In one embodiment, the band portion may include a polyurethane component.

In one embodiment, the band portion may include 5 to 30% by weight of the polyurethane component.

In one embodiment, the band portion may include a polyurethane component to increase elasticity.

In addition to the technical problems of the present disclosure described above, other features and advantages of the present disclosure will be described below, or will be clearly understood by those skilled in the art to which the present disclosure belongs from such description and explanation.

Advantageous Effects

According to the present disclosure described above, the following effects are obtained.

According to the present disclosure, underwear for women with a leak-proof function tightly fitting to a human intergluteal cleft can dramatically prevent the body fluids generated during menstruation from leaking through, by using the band portion including the cleft-fitting band disposed in a corresponding direction along the cleft-fitting region and the support portion supporting the cleft-fitting band.

BRIEF DESCRIPTION OF THE DRAWINGS

FIGS. 6 and 7 are views provided to explain foreign sensation and leak-proof performance according to the length ratio in FIG. 5.

DETAILED DESCRIPTION FOR EMBODYING INVENTION

Figure 1:
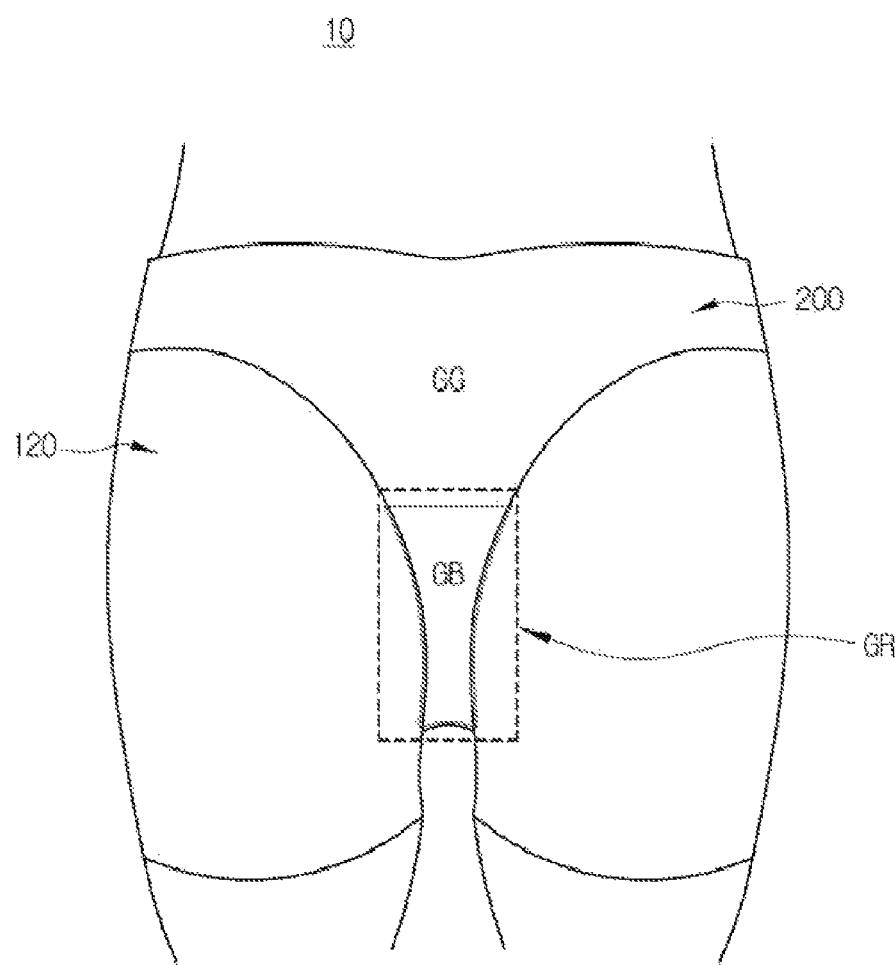
FIG. 1 is a view illustrating underwear according to embodiments of the present disclosure.

It should be noted that, when adding reference numerals to the components shown in the drawings, the same components, whether they are illustrated in the same drawing or different drawings, will be denoted by the same reference numerals if possible.

Meanwhile, the meanings of terms described herein should be understood as follows.

It should be understood that the singular forms include the plural forms as well, unless the context clearly defines otherwise, and the scope of the present disclosure should not be limited by these terms.

It should be understood that terms "comprise" or "have" do not preclude the presence or addition of one or more other features, numbers, steps, operations, components, parts, or combinations thereof.

Hereinafter, preferred embodiments of the present disclosure designed to solve the above problems will be described in detail with reference to the accompanying drawings.

Figure 2:
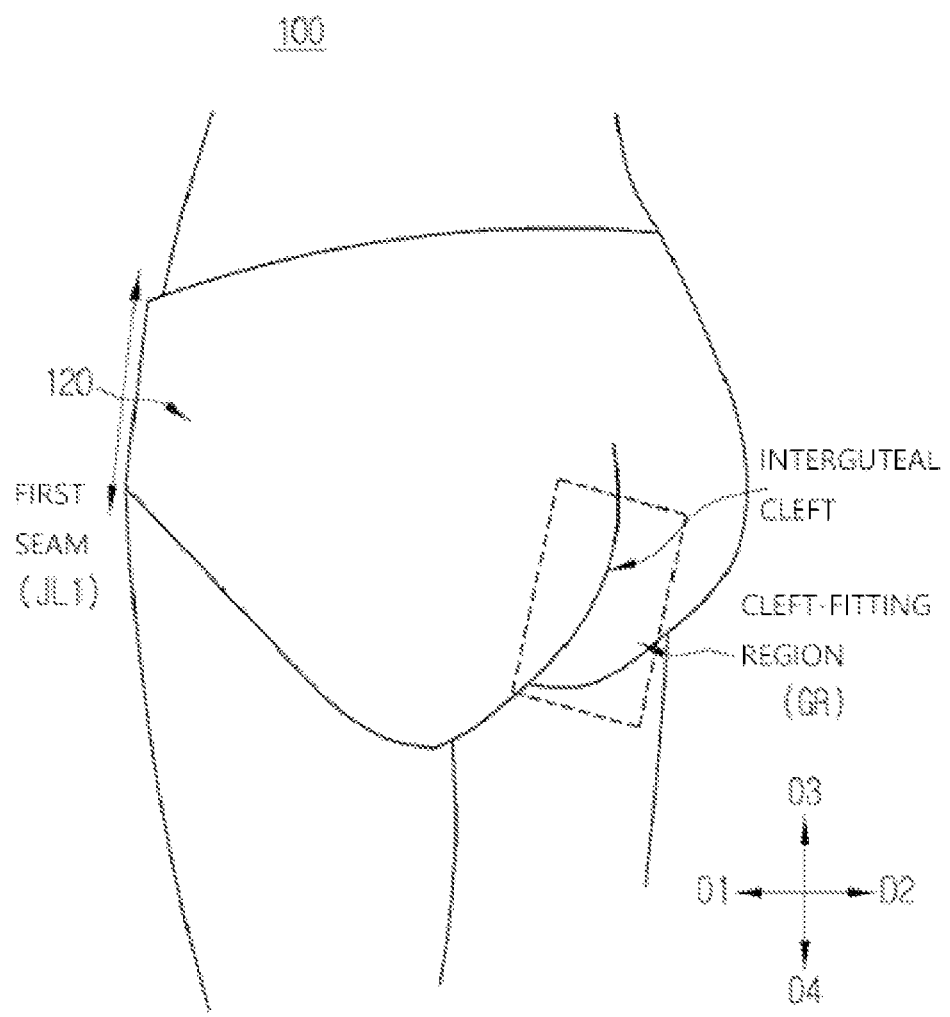
FIG. 2 is a view provided to explain an underwear portion included in the underwear of FIG. 1.
Figure 3:
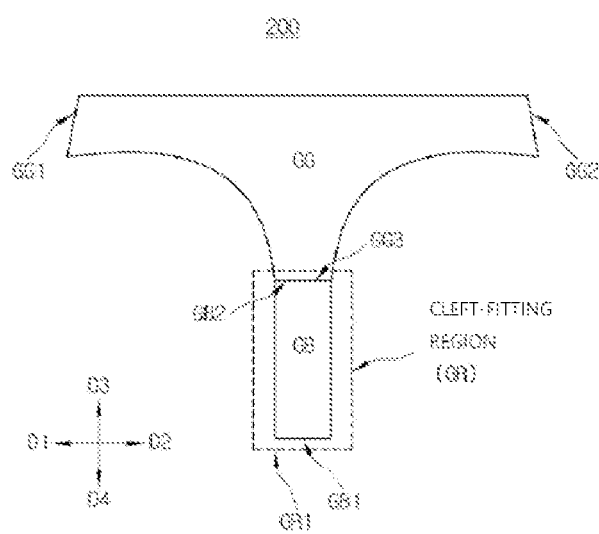
FIG. 3 is a view provided to explain a band portion included in the underwear of FIG. 1.

FIG. 1 is a view illustrating underwear according to embodiments of the present disclosure, FIG. 2 is a view provided to explain an underwear portion included in the underwear of FIG. 1, and FIG. 3 is a view provided to explain a band portion included in the underwear of FIG. 1.

Referring to FIGS. 1 to 3, underwear 10 according to the present disclosure may include an underwear portion 100 and a band portion 200. The underwear portion 100 may include a back side 120 as an opposite side of a front side 110, and the back side 120 may include a cleft-fitting region GR that deforms to conform to the shape of a intergluteal cleft and fits tightly thereto after underwear is worn. For example, the intergluteal cleft may refer to a crack formed between both buttocks near the anus. The cleft-fitting region GR may be a predetermined constant region formed along the intergluteal cleft, and the length and width of the cleft-fitting region GR may be determined so as to provide the wearer with maximum fitting with the least foreign sensation. In one embodiment, the cleft-fitting region GR may be configured with a contractible portion SB so as to be tightly fit to the intergluteal cleft. For example, the contractible portion SB may be formed by a mechanical or chemical shrinkage processing, or by pleating, in which the pleats may include shirring pleats, gathered pleats, dart pleats, politz pleats, ribbed pleats, mechanical pleats, pleats caused by contractible or elastic bands, and combinations thereof.

The band portion 200 may include a cleft-fitting band GB disposed in a corresponding direction along the cleft-fitting region GR and a support portion GG supporting the cleft-fitting band GB. The cleft-fitting band GB may be disposed on the cleft-fitting region GR so that the cleft-fitting region GR can fit more tightly to the intergluteal cleft. In addition, the support portion GG may span the waist to generate tension to pull the cleft-fitting band GB. The support portion GG may be connected to the cleft-fitting band GB so that the cleft-fitting band GB fits more tightly to the cleft-fitting region GR, thereby preventing body fluids from leaking out of the underwear portion 100.

For example, the cleft-fitting band GB may include a first cleft-fitting end GB1 and a second cleft-fitting end GB2, in which the first cleft-fitting end GB1 may be disposed in a fourth direction D4 relative to the center of the cleft-fitting band GB, and the second cleft-fitting end GB2 may be disposed in a third direction D3 relative to the center of the cleft-fitting band GB. Further, the support portion GG may include a first support end GG1, a second support end GG2, and a third support end GG3. The first support end GG1 may be disposed in a first direction D1 relative to the support portion GG, and the second support end GG2 may be disposed in a second direction D2 relative to the support portion GG. In addition, the third support end GG3 may be disposed in a fourth direction D4 relative to the support portion GG.

In one embodiment, one end of the cleft-fitting band GB may be attached to and detached from one end of the cleft-fitting region GR. For example, one end of the cleft-fitting band GB may be the first cleft-fitting end GB1, and one end of the cleft-fitting region GR may be a first cleft-fitting region end GR1. The first cleft-fitting end GB1 may be attachable to and detachable from the first cleft-fitting region end GR1 disposed in the fourth direction D4 relative to the cleft-fitting region GR.

A first end of the support portion GG may be attached to and detached from a first seam JL1 where the front side 110 and the back side 120 of the underwear portion 100 meet, and a second end of the support portion GG may be attached to and detached from a second seam JL2 where the front side 110 and the back side 120 of the underwear portion 100 meet. For example, the first end of the support portion GG may be the first support end GG1, and the second end of the support portion GG may be the second support end GG2. The front side 110 of the underwear portion 100 and the back side 120 of the underwear portion 100 meet each other, forming a line which may be a seam. The seams formed as the front side 110 and the back side 120 meet may be the first seam JL1 and the second seam JL2. In this case, the first support end GG1 may be attachable to and detachable from the first seam JL1, and the second support end GG2 may be attachable to and detachable from the second seam JL2 formed on the opposite side of the first seam JL1. In this example, a detachable member used for the attachment and detachment function may include coupling members of various materials and forms including Velcro, zippers, and hooks and snap buttons.

The underwear for women for tight fitting with a leak-proof function according to the present disclosure can dramatically prevent the body fluids generated during menstruation from leaking through, by using the band portion 200 that includes the cleft-fitting band GB disposed in a corresponding direction along the cleft-fitting region GR and the support portion GG supporting the cleft-fitting band GB, and in addition, it is possible to attach the band portion 200 to the underwear portion 100 and use the same during the menstrual period, and detach the band portion 200 when the menstrual period has elapsed.

Figure 4:
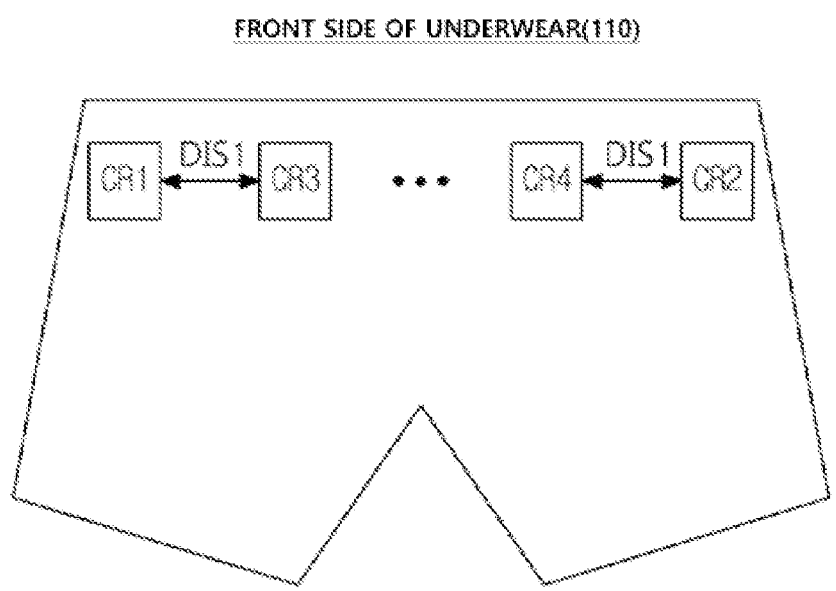
FIG. 4 is a view provided to explain one embodiment of the underwear of FIG. 1.

FIG. 4 is a view provided to explain one embodiment of the underwear of FIG. 1.

Referring to FIGS. 1 to 4, the front side 110 may include a plurality of coupling regions to and from which the first end of the support portion GG and the second end of the support portion GG are attached and detached. For example, the front side 110 of the underwear portion 100 may include a plurality of coupling regions, and the plurality of coupling regions may include a first coupling region CR1, a second coupling region CR2, a third coupling region CR3, and a fourth coupling region CR4. The first end of the support portion GG may be the first support end GG1, and the second end of the support portion GG may be the second support end GG2. The first support end GG1 may be attached to and detached from the first coupling region CR1, and the second support end GG2 may be attached to and detached from the second coupling region CR2. The user may attach the first support end GG1 to the third coupling region CR3 and attach the second support end GG2 to the fourth coupling region CR4 to further tighten the cleft-fitting band GB. In this example, the interval between the first coupling region CR1 and the third coupling region CR3 may be a first interval D1S1, and the interval between the second coupling region CR2 and the fourth coupling region CR4 may also be the first interval D1S1.

Figure 5:
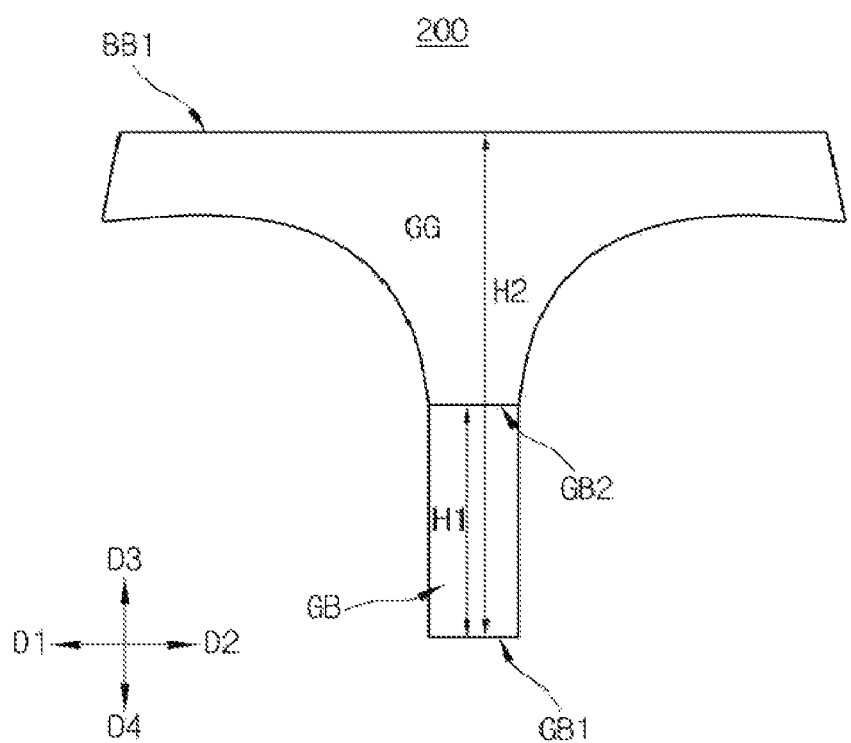
FIG. 5 is a view provided to explain another embodiment of the underwear of FIG. 1.

FIG. 5 is a view provided to explain another embodiment of the underwear of FIG. 1, and FIGS. 6 and 7 are views provided to explain foreign sensation and leak-proof performance according to the length ratios of FIG. 5.

Referring to FIGS. 1 to 7, a foreign sensation score EP indicating a degree of foreign sensation may vary depending on a ratio between a length from one end of the cleft-fitting band GB to one end of the band portion 200 in the third direction D3, and a length of the cleft-fitting band GB. For example, the one end of the cleft-fitting band GB may be the first cleft-fitting end GB1, the length from the first cleft-fitting end GB1 to one end BB1 of the band portion 200 in the third direction D3 may be a second length H2, and the length of the cleft-fitting band GB may be a first length H1. Depending on the ratio between the first length H1 and the second length H2, the foreign sensation score EP indicating the degree of foreign sensation the wearer of the underwear 10 may have in the cleft-fitting region GR may be vary. If the ratio between the first length H1 and the second length H2 is in a first range, the foreign sensation score EP may be 15 points, and if the ratio between the first length H1 and the second length H2 is in a second range, the foreign sensation score EP may be 20 points. Further, if the ratio between the first length H1 and the second length H2 is in a third range, the foreign sensation score EP may be 20 points. The foreign sensation score EP may represent the degree of feeling of the underwear fit in the intergluteal cleft after underwear is worn, and the higher the foreign sensation score, the better the comfort.

In addition, a leak-proof score SP, which represents the ability to prevent the leak of body fluids may vary depending on a ratio between the length from one end of the cleft-fitting band GB to one end of the band portion 200 in the third direction D3, with respect to the length of the cleft-fitting band GB. For example, if the ratio between the first length H1 and the second length H2 is in a first range, the leak-proof score SP may be 20 points, and if the ratio between the first length H1 and the second length H2 is in a second range, the leak-proof score SP may be 20 points. Further, if the ratio between the first length H1 and the second length H2 is in a third range, the leak-proof score SP may be 10 points. In addition, in one embodiment, a comfort score CP indicating a degree of comfort when wearing the entire underwear may vary depending on the ratio between the length from one end of the cleft-fitting band GB to one end of the band portion 200 in the third direction D3, and the length of the cleft-fitting band GB. The leak-proof score SP may represent, by scores, the degree of fitting to the intergluteal cleft after underwear is worn, and the higher the leak-proof score, the better the fitting. The comfort score CP represent the overall degree of comfort experienced after the underwear is worn, and the higher the score, the higher the comfort.

In one embodiment, a value obtained by dividing the length from one end of the cleft-fitting band GB to one end of the band portion 200 in the third direction D3 by the length of the cleft-fitting band GB may be between 2 and 3.

Hereinafter, the present disclosure will be described in more detail with reference to the following examples and comparative examples. However, the following examples are for the purposes of illustrating the present disclosure only.

Tests were conducted on the underwear 10 manufactured according to the examples and comparative examples on 60 adult women.

TABLE 1

| Score Type | Example 1 | Comparative Example 1 | Comparative Example 2 | Unit: points Comparative Example 3 |
|---|---|---|---|---|
| Ratio (H2/H1) | 2-3 | 1-2 | 3-4 | 4-5 |
| Foreign Sensation (EP) | 20 | 20 | 15 | 10 |
| Leak-proof (SP) | 20 | 10 | 20 | 20 |
| Comfort (CP) | 20 | 18 | 15 | 12 |

(10: Very bad, 12: Bad, 15: Fair, 18: Good, 20: Very good)

Underwear of [Example 1]

Underwear manufactured with a ratio (H2/H1) between the first length H1 and the second length H2 in a range of 2-3

Underwear of [Comparative Example 1]

Underwear manufactured with a ratio (H2/H1) between the first length H1 and the second length H2 in a range of 1-2

Underwear of [Comparative Example 2]

Underwear manufactured with a ratio (H2/H1) between the first length H1 and the second length H2 in a range of 3-4.

Underwear of [Comparative Example 3]

Underwear manufactured with a ratio (H2/H1) between the first length H1 and the second length H2 in a range of 4-5

Quality Characteristics

From the comparison results obtained according to Example 1, it was confirmed that the underwear 10 with the ratio H2/H1 between the first length H1 and the second length H2 in a range of 2-3 exhibited higher qualities compared to the comparative examples in terms of foreign sensation, leak-proof effect, and comfort.

In one embodiment, the band portion 200 may include a polyurethane component. Further, in one embodiment, the band portion 200 may include 5 to 30% of polyurethane component. The elasticity of a fiber refers to a quality of the fiber to recover its original length once the external force that stretches it disappears, and elastic modulus refers to the percentage of the recovered length with respect to the stretched length, and the band portion may include the polyurethane component in a range of 5 to 30% to increase the elastic modulus and maintain shape stability.

Figure 8:
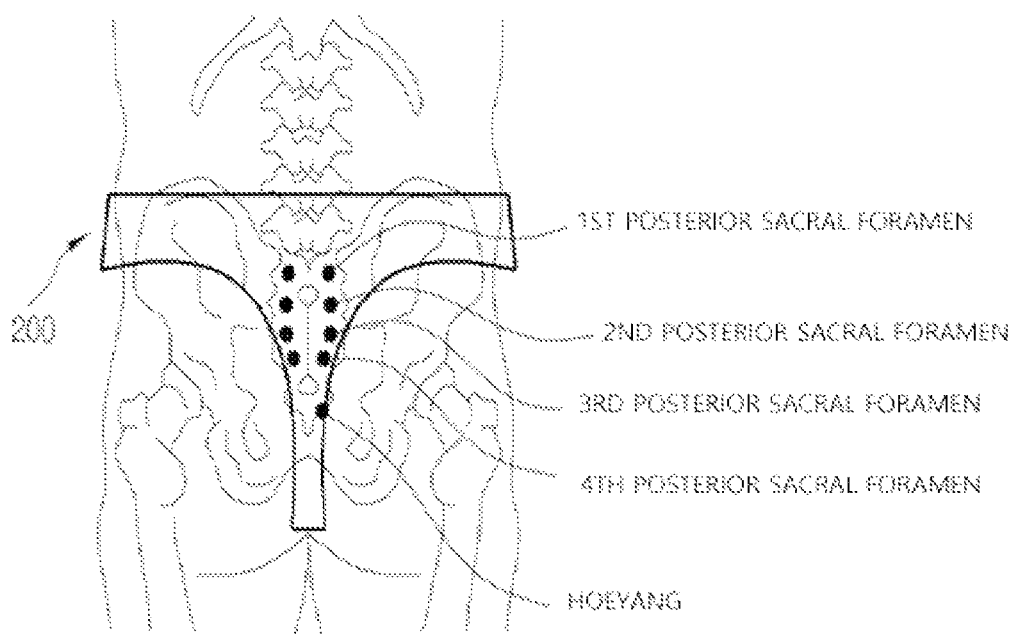
FIG. 8 is a view provided to explain the effect of the underwear of FIG. 1

The underwear for women for tight fitting with a leak-proof function according to the present disclosure can dramatically prevent the body fluids generated during menstruation from leaking through, by using the band portion 200 that includes the cleft-fitting band GB disposed in a corresponding direction along the cleft-fitting region GR and the support portion GG supporting the cleft-fitting band GB FIG. 8 is a view provided to explain the effect of the underwear of FIG. 1

Referring to FIGS. 1 to 8, the underwear 10 according to the present disclosure can be used to increase the force of holding various pads such as sanitary napkins, pantie liners, incontinence pads, etc. securely in position, by pressing a concave area along the boundary between the upper part of the hip (upper gluteal region) and the lower part of the waist (lower abdominal region) curves. In addition, since the band portion 200 can automatically press and stimulate acupuncture points, the effect of relieving menstrual pain can be expected. By naturally stimulating acupuncture points, the band portion 200 can improve blood circulation and be effective for menstrual pain, headaches, stiff shoulders, etc.

Figure 9:
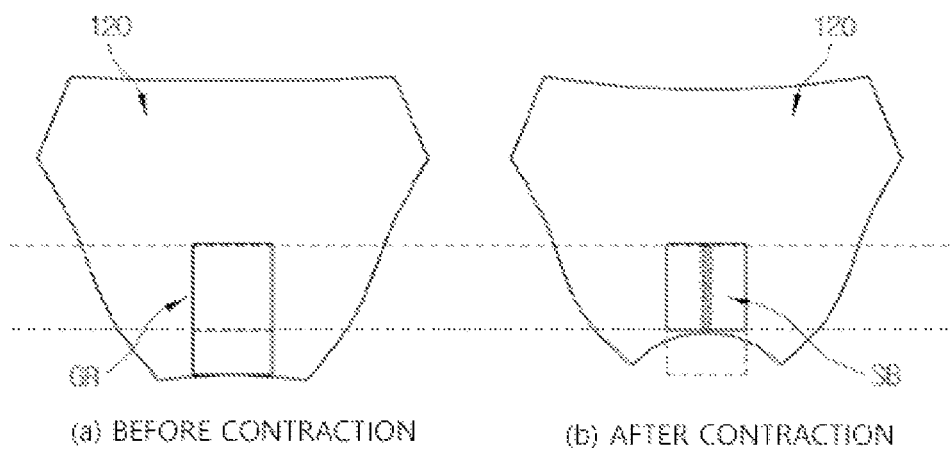
FIGS. 9 and 10 are views provided to explain a contractible portion of a cleft-fitting region included in the underwear of FIG. 1.
Figure 10:
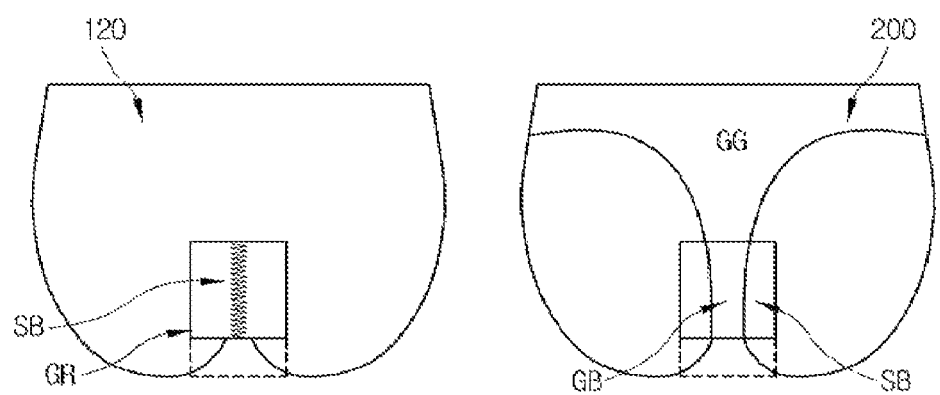

FIGS. 9 and 10 are views provided to explain a contractible portion of the cleft-fitting region included in the underwear of FIG. 1.

Referring to FIGS. 1 to 10, in one embodiment, the contractible portion SB of the cleft-fitting region GR may be contracted by 20 to 50%, or preferably 30 to 40% compared to before the contractible portion SB was formed. For example, if the contraction rate is less than 20%, the fit to the intergluteal cleft may be lowered, resulting in a decreased leak-proof score SP, and if the contraction rate is greater than 50%, the excessive fit may increase the foreign sensation score EP, which may be undesirable. For example, the contractible portion SB of the cleft-fitting region GR may be 10 cm before pleating. In this case, when the cleft-fitting region GR is pleated, the contractible portion SB of the cleft-fitting region GR may be contracted to between 6 and 7 cm.

The fit may be determined according to the degree of contraction of the cleft-fitting region GR, and the higher the contraction rate, the higher the fit, and the lower the contraction rate, the lower the fit. In addition, the higher fit can increase foreign sensation and therefore decrease the foreign sensation score EP, and the lower fit can decrease foreign sensation and therefore increase the foreign sensation score EP.

On the other hand, the higher contraction rate can increase the fit, which increases the leak-proof performance and thus the leak-proof score SP, and the lower contraction rate can decrease the fit, which decreases the leak-proof performance and thus the leak-proof score SP.

Therefore, in order to achieve sufficient leak-proof performance, it may be important to have a contraction rate with which it is possible to minimize foreign sensation and also increase a fit.

The length of the band portion 200 may depend on the contraction rate of the cleft-fitting region GR, and may be adjusted in response to the reduced length, and may be equal to, or about 2 to 5% shorter than, the length from the end of the shrunken cleft-fitting region GR to the waist.

The band portion 200 may serve to assist in increasing the fit of the cleft-fitting region GR, and since tension acts on the one end of the cleft-fitting band GB in the third direction D3, and tension acts on the waist in both the first direction D1 and the second direction D2 from the support portion GG, the load of the sanitary napkin that is heavy with body fluids after underwear is worn can be better supported than when the sanitary napkin includes only the cleft-fitting region GR.

[Example—Contraction Rate]

Comparison of comfort and leak-proof effect for contraction rate of the cleft-fitting region

TABLE 2

| Score Type | Example 2 | Comparative Example 4 | Comparative Example 5 | Comparative Example 6 |
|---|---|---|---|---|
| Elastic Modulus (%) | 30-40 | 15-20 | 50-55 | 55-60 |
| Foreign Sensation (EP) | 20 | 20 | 12 | 10 |
| Leak-proof (SP) | 20 | 12 | 20 | 20 |
| Comfort (CP) | 20 | 18 | 12 | 10 |

(10: Very bad, 12: Bad, 15: Fair, 18: Good, 20: Very good)

Unit: points

Underwear of [Example 2]
Underwear with a contraction rate of 30 to 40% in the contractible portion of the cleft-fitting region
Underwear of [Comparative Example 4]
Underwear with a contraction rate of 15 to 20% in the contractible portion of the cleft-fitting region
Underwear of [Comparative Example 5]
Underwear with a contraction rate of 50 to 55% in the contractible portion of the cleft-fitting region
Underwear of [Comparative Example 6]
Underwear with a contraction rate of 55 to 60% in the contractible portion of the cleft-fitting region
Quality Characteristics From the comparison results obtained according to Example 2, it was confirmed that the underwear 10 having a contraction rate of 30 to 40% in the contractible portion of the cleft-fitting region exhibited higher qualities compared to the comparative examples in terms of foreign sensation, leak-proof effect, and comfort.

Figure 11:
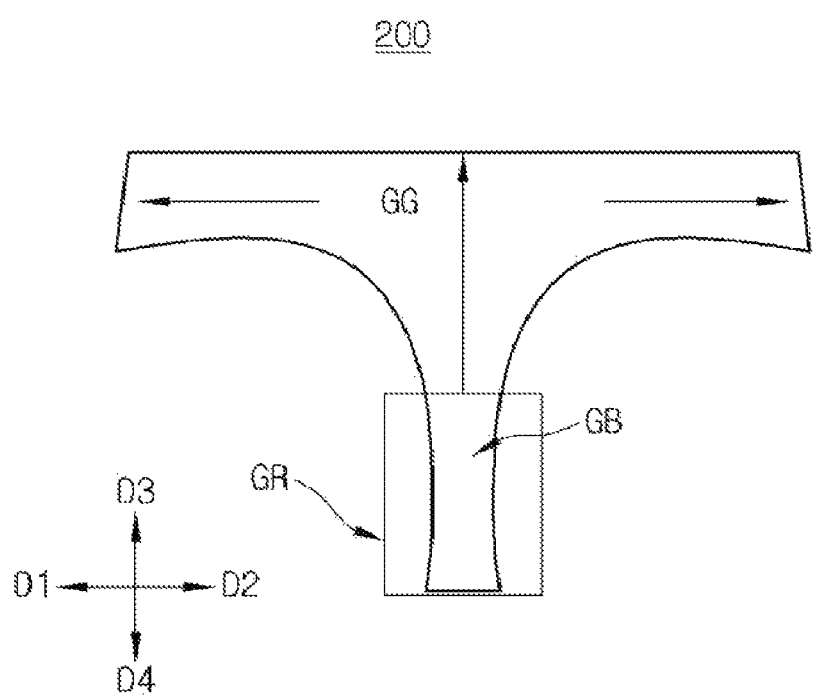
FIG. 11 is a view provided to explain a force acting on the band portion included in the underwear of FIG. 1.
Figure 12:
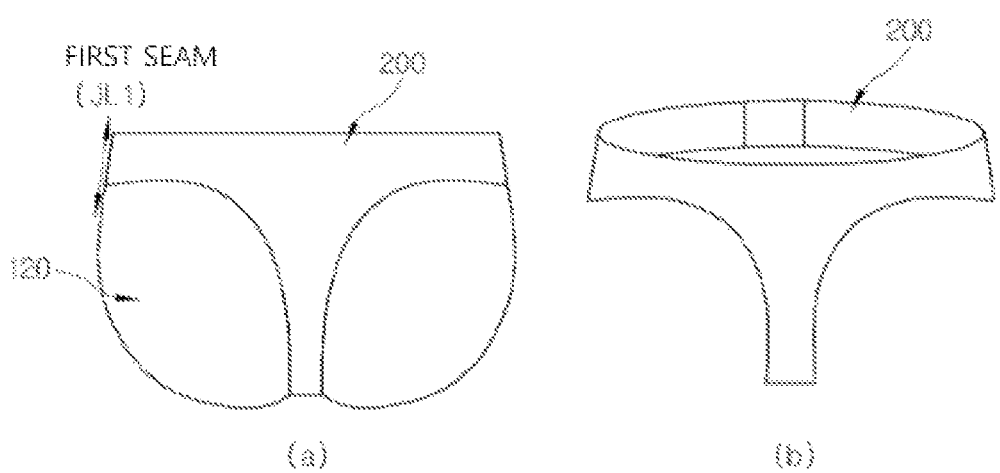
FIG. 12 is a view provided to explain a method of attaching and detaching the band portion included in the underwear of FIG. 1.

FIG. 11 is a view provided to explain a force acting on the band portion included in the underwear of FIG. 1, and FIG. 12 is a view provided to explain a method of attaching and detaching the band portion included in the underwear of FIG. 1.

Referring to FIGS. 1 to 12, the band portion 200 may include the support portion GG and the cleft-fitting band GB. When the underwear 10 according to the present disclosure is worn, tension can act on the support portion GG in both the first direction D1 and the second direction D2, and tension can act on the cleft-fitting band GB in the third direction D3. The underwear 10 according to the present disclosure may include the underwear portion 100 and the band portion 200. The band portion 200 may be attached to and detached from the underwear portion 100 in various ways. For example, as shown in FIG. 12A, the band portion 200 may be engaged with the first seam JL1 and thus attached to the underwear portion 100, or as shown in FIG. 12B, the band portion 200 may be attached to the underwear portion 100 in such a way that the support portion GG included in the band portion 200 is wrapped around the entire waist and engaged in front.

In addition to the technical problems of the present disclosure described above, other features and advantages of the present disclosure will be described below, or will be clearly understood by those skilled in the art to which the present disclosure belongs from such description and explanation.

[Description of the Reference Numerals]

| | |
|---|---|
| 10: underwear | 100: underwear portion |
| 200: band portion | 110: front side |
| 120: back side | |

The invention claimed is:

1. An underwear comprising:
an underwear portion including a back side as an opposite side to a front side, the back side including a cleft-fitting region configured to deform to conform to a shape of an intergluteal cleft and tightly fits thereto;
a band portion including a cleft-fitting band disposed in a corresponding direction along the cleft-fitting region, and a support portion supporting the cleft-fitting band,
wherein the cleft-fitting region includes a contractible portion formed therein so as to allow tight fit to the intergluteal cleft,
wherein one end of the cleft-fitting band is attached to and detached from one end of the cleft-fitting region, a first end of the support portion is attached to and detached from a first seam where the front side and the back side of the underwear portion meet, and a second end of the support portion is attached to and detached from a second seam where the front side and the back side of the underwear portion meet.

2. The underwear according to claim 1, wherein the front side includes a plurality of coupling regions to and from which the first end of the support portion and the second end of the support portion are attached and detached.

3. The underwear according to claim 1, wherein a foreign sensation score indicating a degree of foreign sensation varies depending on a ratio between a length from one end of the cleft-fitting band to one end of the band portion in a third direction, and a length of the cleft-fitting band, wherein the third direction is a direction perpendicular to a first direction.

4. The underwear according to claim 1, wherein a leak-proof score indicating a degree of ability to prevent leaks of body fluids varies depending on a ratio between a length from one end of the cleft-fitting band to one end of the band portion in a third direction, and a length of the cleft-fitting band, wherein the third direction is a direction perpendicular to a first direction.

5. The underwear according to claim 1, wherein a value obtained by dividing a length from one end of the cleft-fitting band to one end of the band portion in a third direction by a length of the cleft-fitting band is between 2 and 3, wherein the third direction is a direction perpendicular to a first direction.

6. The underwear according to claim 1, wherein the band portion includes a polyurethane component.

7. The underwear according to claim 6, wherein the band portion includes 5 to 30% of the polyurethane component.

8. The underwear according to claim 1, wherein the contractible portion of the cleft-fitting region is contracted by 30 to 40% compared to before the contractible portion is formed.

* * * * *